United States Patent
Farida et al.

(10) Patent No.: US 10,513,490 B2
(45) Date of Patent: Dec. 24, 2019

(54) METHOD FOR PRODUCING ACYLSULFAMOYLBENZAMIDES

(71) Applicant: BAYER CROPSCIENCE AKTIENGESELLSCHAFT, Monheim am Rhein (DE)

(72) Inventors: Taraneh Farida, Pulheim-Geyen (DE); Michael Esser, Leverkusen (DE); Hubertus Stakemeier, Bergisch Gladbach (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 15/565,067

(22) PCT Filed: Apr. 4, 2016

(86) PCT No.: PCT/EP2016/057322
§ 371 (c)(1),
(2) Date: Oct. 6, 2017

(87) PCT Pub. No.: WO2016/162299
PCT Pub. Date: Oct. 13, 2016

(65) Prior Publication Data
US 2018/0118670 A1    May 3, 2018

(30) Foreign Application Priority Data
Apr. 8, 2015   (EP) ..................................... 15162810

(51) Int. Cl.
*C07C 303/40* (2006.01)

(52) U.S. Cl.
CPC ........ *C07C 303/40* (2013.01); *C07C 2601/02* (2017.05)

(58) Field of Classification Search
None
See application file for complete search history.

(56) References Cited

U.S. PATENT DOCUMENTS

| | | | |
|---|---|---|---|
| 9,725,409 B2 * | 8/2017 | Farida | C07C 303/40 |
| 2005/0004372 A1 * | 1/2005 | Pazenok | C07C 303/40 548/530 |
| 2017/0305845 A1 * | 10/2017 | Farida | C07C 303/40 |

FOREIGN PATENT DOCUMENTS

| | | |
|---|---|---|
| CN | 101838227 A | 9/2010 |
| WO | 99/16744 A1 | 4/1999 |
| WO | 2005/000797 A1 | 1/2005 |
| WO | 2015/052156 A1 | 4/2015 |

OTHER PUBLICATIONS

King ("pH Optimization of Nucleophilic Reactions in Water" J. Am. Chem. Soc. 1992, 114, p. 3028) (Year: 1992).*
Rajput ("N-Acylation in non-aqueous and aqueous medium-method of amide synthesis in non-peptide compounds" Der Pharma Chemica, 2011, 3(3), p. 409-421) (Year: 2011).*
International Search Report of International Patent Application No. PCT/EP2016/057322 dated Jun. 23, 2016.

* cited by examiner

*Primary Examiner* — Amy C Bonaparte
(74) *Attorney, Agent, or Firm* — McBee Moore Woodward & Vanik IP, LLC

(57) ABSTRACT

The invention relates to a method for producing compounds of formula (Ia), in particular to a method for producing N-[4-(cyclopropylcarbamoyl)phenylsulfonyl]-2-methoxybenzamide.

14 Claims, No Drawings

METHOD FOR PRODUCING ACYLSULFAMOYLBENZAMIDES

CROSS-REFERENCE TO RELATED APPLICATIONS

This application is a National Stage entry of International Application No. PCT/EP2016/057322, filed 4 Apr. 2016, which claims priority to European Patent Application No. 15162810.4, filed 8 Apr. 2015.

BACKGROUND

Field

The invention relates to a process for preparing acylsulfamoylbenzamides; more particularly, the invention relates to an improved process for preparing N-[4-(cyclopropylcarbamoyl)phenylsulfonyl]-2-methoxybenzamide.

Description of Related Art

N-[4-(Cyclopropylcarbamoyl)phenylsulfonyl]-2-methoxybenzamide (or alternatively: N-[4-(cyclopropylcarbamoyl)phenylsulfonyl]-o-anisamide) is also referred to by the common name of cyprosulfamide. Cyprosulfamide is used as a safener in agriculture in combination with a herbicide, or with a plurality of different herbicides. A safener serves to improve the selectivity of the herbicides used with respect to the crop plants of the crop being treated in each case. The term "selectivity" refers to the crop plant compatibility of a herbicide.

Document WO 99/16744 discloses acylsulfamoylbenzamide derivatives and the preparation and use thereof as a safener. However, the preparation processes disclosed in WO 99/16744 relate to the laboratory scale and are found not to be particularly suitable for the industrial preparation of the compounds.

Document CN 101 838 227 A discloses constitutional isomers of cyprosulfamide and an alternative process for preparation thereof.

A two-stage process which has been developed for preparation of acylsulfamoylbenzamides on the industrial scale is known from document WO 2005/000797 A1.

A further two-stage process which also includes the preparation of an amide chloride precursor required for the cyprosulfamide synthesis and which can alternatively also be employed as a one-stage process (i.e. without prior isolation of the precursor (intermediate) in the context of a one-pot synthesis is described in international patent application PCT/EP2014/071388 (WO 2015/052156 A1).

The process described in the aforementioned patent application WO 2015/052156 A1 is likewise suitable for preparation of acylsulfamoylbenzamides (Ia) on the industrial scale, without using an organic solvent. In other words, the conversion (reaction) of an amide chloride with a secondary amine as reactants proceeds in an aqueous solution without the use of organic solvents.

The filing date of WO 2015/052156 A1 is prior to the filing date of the present application, although patent application WO 2015/052156 A1 was yet to be published at the filing date of the present application.

Amination—Option I

In a process option known according to Schotten-Baumann (option I), the initial charge contains both reactants, i.e. the amide chloride of the formula (II) and the secondary amine of the formula RRNH, while aqueous alkali metal hydroxide solution (sodium hydroxide solution or potassium hydroxide solution) is added dropwise over the course of the reaction.

Without an organic solvent, however, the reaction regime known according to option I is not possible. Without organic solvent, the reaction mixture forms a solid, barely stirrable block, since a small amount of liquid amine in terms of mass encounters a large amount of solid amide chloride. For ecological and economic reasons, however, the aim is to avoid the use of organic solvents in industrial scale production.

Amination—Option II

The use of water as diluent would be possible in principle in the case of the process regime according to option I, but would hydrolyse the amide chloride of the formula (II) in an unwanted side reaction and lead to poorer yields as a result.

In a second alternative reaction regime known according to Schotten-Baumann (option II), the secondary amine of the formula RRNH is initially charged in an auxiliary base (e.g. NaOH or KOH), while the amide chloride of the formula (II) is metered in in solid form.

The simultaneous initial charging of the two bases does not disrupt the course of the reaction because amines are stronger nucleophiles than the hydroxide ions in the alkali metal hydroxide solution, meaning that the hydroxide ions from the alkali metal hydroxide solution do not affect the reaction but serve merely to neutralize the acid released.

Nevertheless, the employment of the aforementioned option II for preparation of compounds of the formula (Ia) specified below on the industrial scale was not found to have adequate efficiency. The pH of the reaction mixture in the reaction regime according to option II is in the range from pH 13 to 14.

Amination—Option III

A further alternative reaction regime (option III) is described by the abovementioned international application PCT/EP2014/071388 by Farida et al. In the case of this option III, a secondary amine is initially charged together with the amide chloride of the formula (II) specified below in an aqueous NaOH solution.

Surprisingly, in the case of the process regime according to option III for preparation of acylsulfamoylbenzamides, high yields are achieved even without the use of an organic solvent.

Compared to the previously known reactions (options I and II), it is thus a feature of the process according to the patent application PCT/EP2014/071388 (option III) that no organic solvent is used for preparation of the target compound of the formula (Ia), meaning that the reaction is effected in an aqueous solution alone.

In the context of the present invention, which involves the implementation of the process disclosed in patent application PCT/EP2014/071388 in the chemical industry (i.e. industrial scale preparation), however, it has been recognized that initial charging of the stoichiometric amount of a secondary amine of the formula RRNH in full at the very start of the reaction can result in an unwanted increase in the pH.

In addition, it has been recognized that the unwanted increase in the pH after addition of the amide chloride (II) later in the reaction brings about the formation of the corresponding acid of the amide chloride (II). The unwanted acid of the amide chloride (II) is 4-[[(2-methoxybenzoyl)amino]sulfonyl]benzoic acid, which forms the corresponding salt in the presence of the alkali metal ions (sodium ions or potassium ions). This salt no longer reacts to a sufficient degree with the secondary amine of the formula RRNH to give the end product. This leads to high yield losses.

Because of the large production volumes that are typically the aim when a process is employed on the industrial scale, even apparently minor improvements to a process may be very relevant for economic and also for environmental reasons.

Against this background, the problem addressed by the invention was that of providing an improved alternative process for preparing acylsulfamoylbenzamides, and the alternative process is to feature high robustness with simultaneously high yields.

SUMMARY

The problem is solved by a process for preparing compounds of the formula (Ia)

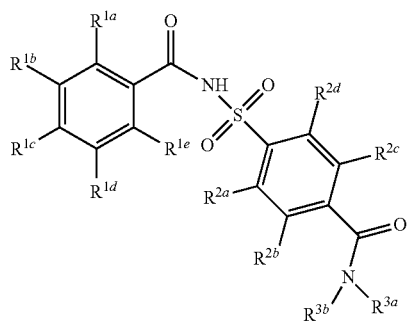

in which $R^{1a}$ to $R^{1e}$ and $R^{2a}$ to $R^{2d}$ are each independently selected from the group consisting of hydrogen, halogen, $(C_1-C_6)$-alkyl, $(C_1-C_6)$-haloalkyl, $(C_1-C_6)$-alkoxy, $(C_3-C_7)$-cycloalkyl, $(C_1-C_6)$-alkylthio, $(C_3-C_7)$-cycloalkylthio, $S(O)_q$—$(C_1-C_6)$-alkyl with q=0, 1 or 2, $(C_1-C_6)$-alkylcarbonyl, —CO-aryl, cyano and nitro or in which two adjacent $R^{1a}$ to $R^{1e}$ radicals in each case form a —O—CH$_2$CH$_2$— radical, and $R^{3a}$ is selected from the group consisting of hydrogen and the following radicals: $(C_1-C_6)$-alkyl, $(C_1-C_6)$-haloalkyl, $(C_3-C_7)$-cycloalkyl, $(C_1-C_6)$-alkoxy, $(C_1-C_6)$-alkylthio, $(C_3-C_7)$-cycloalkylthio, —(CH$_2$)p-heterocyclyl, where these are each unsubstituted or substituted by one or more substituents selected from the group consisting of halogen, $(C_1-C_6)$-alkyl, $(C_1-C_6)$-haloalkyl, $(C_1-C_6)$-alkoxy, cyano and nitro, and $R^{3b}$ is selected from the group consisting of hydrogen and the following radicals: $(C_1-C_6)$-alkyl, $(C_2-C_6)$-alkenyl, $(C_2-C_6)$-alkynyl, $(C_1-C_6)$-alkoxy, $(C_2-C_6)$-alkenyloxy, —(CH$_2$)p-heterocyclyl, where these are each unsubstituted or substituted by one or more substituents selected from the group consisting of halogen, $(C_1-C_4)$-alkoxy and $(C_1-C_4)$-alkylthio, or $R^{3a}$ and $R^{3b}$ together with the connecting nitrogen atom form a 3- to 8-membered, saturated or unsaturated ring, by reacting a compound of the formula (II)

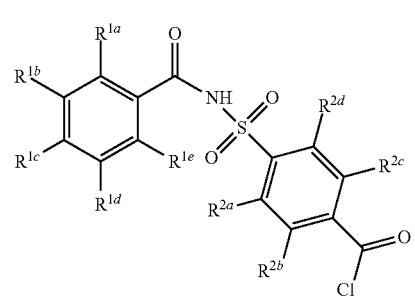

with an amine of the formula $R^{3a}R^{3b}NH$ in which the $R^{3a}$ and $R^{3b}$ radicals are each as defined above, in aqueous solution, wherein the pH is regulated by initially charging only a portion of the amine of the formula $R^{3a}R^{3b}NH$ in water at the start of the reaction, and adding the remaining amount of the amine of the formula $R^{3a}R^{3b}NH$ to the reaction mixture over the course of the reaction in one or more steps.

DETAILED DESCRIPTION OF A PREFERRED EMBODIMENT

The process according to the present invention builds on the use of water as solvent according to the abovementioned option III, in which case the initial reaction charge in the process of the invention does not contain any alkali metal hydroxide solution.

Compared to the prior art according to options I and II, it is thus a feature of the process of the invention that the solvent used is water and not an organic solvent.

Compared to the process described in international patent application PCT/EP2014/071388, the process of the invention is novel because the initial charge in the reaction in the process of the invention does not contain any alkali metal hydroxide solution, for example sodium hydroxide solution. Instead, in the process of the invention, a small amount of the amine of the formula $R^{3a}R^{3b}NH$ is initially charged in water, where the $R^{3a}R^{3b}$ radicals are as defined in the aforementioned formula (Ia).

The remaining amount of amine is added to the reaction mixture preferably during (simultaneously with) the addition of the amide chloride of the formula (II). In other words, the remaining amount of amine is preferably added in parallel with the addition of the amide chloride.

The effect of the early regulation of the pH in the initial charge of reaction mixture by metered addition of the amine according to teaching of the process of the invention, compared to the processes previously known from WO 99/16744 and from WO 2005/000797 A1, is a considerable improvement in the acylsulfamoylbenzamide yield.

The special feature of this introductory process step, i.e. the initial regulation of the pH in the preparation of cyprosulfamide, is based on the observation of the fact that the chemical structure of the reactant of the formula (II), 4-[[(2-methoxybenzoyl)amino]sulfonyl]benzoyl chloride, has one acidic proton and the chemical structure of the cyprosulfamide end product actually has two acidic protons. For this reason, the hydrolysis sensitivity of both compounds is classified as high. However, this hydrolysis sensitivity is highly dependent on the pH of the solution in which the compounds mentioned are present.

It has been recognized in accordance with the invention that even the initial charging of basic amine of the formula $R^{3a}R^{3b}NH$ can attenuate the hydrolysis sensitivity of the reactant of the formula (II) 4-[[(2-methoxybenzoyl)amino] sulfonyl]benzoyl chloride (and that of the cyprosulfamide formed) to an unexpected degree.

The avoidance or attenuation of the hydrolysis reaction is advantageous because this suppresses the formation of 4-[[(2-methoxybenzoyl)amino]sulfonyl]benzoic acid (present in the reaction solution as a comparatively non-reactive salt because of the presence of alkali metal ions), and thus consequently enables the achievement of higher cyprosulfamide yields.

The invention thus relates to the optimization of the yield and the improvement of the robustness of the process. Because of the comparatively large product volumes in industrial manufacture, even just a small improvement in the yield is of great significance from an economic point of view. An improvement in the purity of the product may also be of great economic significance.

Therefore, the improvement of a process performable on the industrial scale by variation of all reaction parameters in the industrial active ingredient preparation is fundamentally a constant endeavour. However, the variation of the parameters is often, in spite of the systematic approach, not a matter of merely routine trial and error.

Specifically the unexpectedly strong influence of the initial (and of the later) pH regulation by metered addition of the amine on a chemical reaction can often be recognized and explained only retrospectively.

Preference is given to the process of the invention for preparing compounds of the formula (Ia) in which the $R^{1a}$ to $R^{1e}$ and $R^{2a}$ to $R^{2d}$ radicals are independently selected from the group consisting of hydrogen, fluorine, chlorine, bromine,
($C_1$-$C_6$)-alkyl, where the alkyl radical is branched or unbranched and is unsubstituted or substituted by one or more substituents selected from the group consisting of ($C_1$-$C_4$)-alkoxy and ($C_3$-$C_7$)-cycloalkyl,
($C_1$-$C_6$)-haloalkyl, where the alkyl radical is unsubstituted or substituted by one or more substituents selected from the group consisting of fluorine, chlorine, bromine and iodine,
($C_3$-$C_7$)-cycloalkyl, where the cycloalkyl radical is unsubstituted or substituted by one or more substituents selected from the group consisting of ($C_1$-$C_4$)-alkyl and ($C_3$-$C_7$)-cycloalkyl and ($C_1$-$C_4$)-alkoxy,
($C_1$-$C_6$)-alkoxy, where the alkoxy radical is branched or unbranched and is unsubstituted or substituted by one or more substituents selected from the group consisting of ($C_1$-$C_4$)-alkoxy and ($C_3$-$C_7$)-cycloalkyl,
($C_3$-$C_7$)-cycloalkoxy, where the cycloalkoxy radical is unsubstituted or substituted by one or more substituents selected from the group consisting of ($C_1$-$C_4$)-alkyl and ($C_1$-$C_4$)-alkoxy,
($C_1$-$C_6$)-alkylthio, where the alkylthio radical is branched or unbranched and is unsubstituted or substituted by one or more substituents selected from the group consisting of ($C_1$-$C_4$)-alkyl and ($C_1$-$C_4$)-alkoxy,
($C_3$-$C_7$)-cycloalkylthio, where the cycloalkylthio radical is unsubstituted or substituted by one or more substituents selected from the group consisting of ($C_1$-$C_4$)-alkyl and ($C_1$-$C_4$)-alkoxy.

Particular preference is given to a process for preparing compounds of the formula (Ia) in which $R^{1a}$ is selected from the group consisting of unsubstituted ($C_1$-$C_4$)-alkoxy radicals and $R^{1b}$ to $R^{1d}$ and $R^{2a}$ to $R^{2d}$ are each hydrogen.

Very particular preference is given to a process for preparing compounds of the formula (Ia) in which $R^{1a}$ is methoxy (—O—$CH_3$), and $R^{1b}$ to $R^{1d}$ and $R^{2a}$ to $R^{2d}$ are each hydrogen.

Most preferred is a process for preparing compounds of the formula (Ia) in which
$R^{1a}$ is methoxy (—O—$CH_3$) and $R^{1b}$ to $R^{1d}$ and $R^{2a}$ to $R^{2d}$ are each hydrogen and, in the
amine of the formula $R^{3a}R^{3b}NH$, the $R^{3a}$ radical is cyclopropyl and $R^{3b}$ is hydrogen.

The product formed in the aforementioned most preferred process is cyprosulfamide and has the formula (Ib)

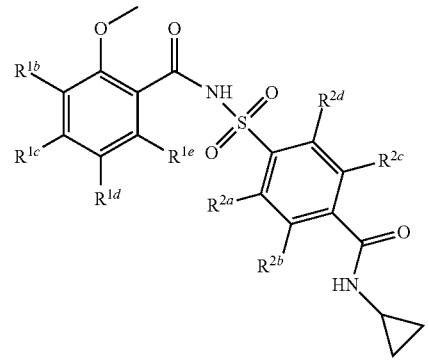

(Ib)

in which
the $R^{1b}$ to $R^{1e}$ and $R^{2a}$ to $R^{2d}$ radicals are each hydrogen.

In a preferred embodiment of the invention, the pH of the initial charge at the start of the reaction is not more than 11.5 (pH≤11.5). This is achieved by the initial charging of an appropriate amount of the amine of the formula $R^{3a}R^{3b}NH$ in water, Only after this initial adjustment of the pH in the initial reaction charge to pH≤11.5 is the reactant of the formula (II) added.

The addition of the amide chloride present in solid form, i.e. of the reactant of the formula (II), to the aqueous amine solution which forms the initial reaction charge may be quantitative. However, the amide chloride (acid chloride) is preferably added by metered addition, i.e. in several steps. Particular preference is given to addition extending over a period of about 4 hours in 20 to 30 steps (portions). In the context of technical production, very particular preference is given to the continuous addition of the amide chloride by means of a metering screw.

According to the teaching of the present invention, the addition of the amine of the formula $R^{3a}R^{3b}NH$ is effected in at least two steps overall.

The first addition step relates to the addition of amine at the start of the reaction, with the aim of adjusting the pH in the initial reaction charge to pH≤11.5. The addition of the remaining amount of the amine of the formula $R^{3a}R^{3b}NH$ is effected either in one step (2-stage addition of amine) or in a plurality of steps (at least 3-stage addition of amine).

The addition of the remaining amount of the amine of the formula $R^{3a}R^{3b}NH$ in a plurality of steps (i.e. at least 3-stage addition of amine) of course also includes the metered addition of the amine in very small amounts, for example by addition of the amine to the reaction mixture using one or more feed lines.

In industrial scale production, very particular preference is given to the continuous addition of the amine in very many steps, for example by the pH-regulated dropwise addition or pumped addition of the amine to the reaction mixture.

In a particularly preferred embodiment of the invention, the addition of the amount of the amine of the formula $R^{3a}R^{3b}NH$ which is not initially charged at the start of the reaction is effected in several steps, such that the pH during the addition in the further course of the reaction is in the range from 7 to 10.5 (pH=7-10.5).

The pH-regulated addition of the amine of the formula $R^{3a}R^{3b}NH$ to the reaction mixture in the course of the at least 3-stage addition of amine is preferably effected until attainment of 1.1 equivalents, based on the amount of amide chloride (acid chloride) initially charged.

It is within the scope of the invention that the subsequent pH-regulated addition of amine is effected by dropwise addition or by pumped addition.

The pH-regulated addition of the amine of the formula $R^{3a}R^{3b}NH$ to the reaction mixture is preferably effected in such a way that the pH during the addition over the further course of the reaction is in the range from 9 to 10.5 (pH=9 to 10.5), or most preferably in the range from 9.0 to 9.6 (pH=9.0 to 9.6).

A pH above the value of 10.5 already has the effect of unwanted carboxylic acid formation, and at pH 13 about 5% of the amide chloride of the formula (II) is already in carboxylic acid form. This has the effect of an unwanted reduction in the yield of the product of the formula (Ia).

In a very particularly preferred embodiment of the invention, the additional use of a base selected from the group consisting of NaOH, KOH, Ca(OH)$_2$ and the group of the tertiary amines, especially triethylamine, is envisaged for regulation of the pH in the reaction mixture (pH regulation), in which case the pH of the reaction mixture is to be stabilized within the range from 8 to 10 by the addition of the base. More particularly, addition of NaOH is supposed to prevent a drop in the pH below the pH of 8, meaning that the target pH which is the aim of addition of NaOH toward the conclusion of the reaction is 8.

The additional base selected from the group consisting of NaOH, KOH, Ca(OH)$_2$ and the group of the tertiary amines is thus not added to the initial reaction charge; instead, the additional base is added to the reaction mixture already containing the desired reactant.

The additional use of a base selected from the group consisting of NaOH, KOH, Ca(OH)$_2$ and the group of the tertiary amines is effected during the reaction, preferably on completion of addition of the amine and after addition of 20% of the amide chloride. Alternatively, the addition of the base can also be effected as a final addition, i.e. on completion of addition of the amide chloride.

Most preferred is the use of NaOH for setting of a pH within the range from 9 to 10 (pH=9 to 10).

It has been found that the final addition of a small amount of an organic solvent, for example of toluene, facilitates the stirrability (and pumpability) of the product which takes the form of a suspension which is difficult to pump.

Thus, a preferred way of conducting the process of the invention comprises the following general process steps together:
   initial charging of water and a small amount of cyclopropylamine (=CPA), such that the pH is max. 11.5, and the preferably parallel
   addition of the amide chloride (solid amount/h) and the amine at pH 7-10.5 until 1.1 equivalents, based on amide chloride, have been attained, and the
final or parallel addition of sodium hydroxide solution to the continuing metered addition of acid chloride.

Solely to support the enablement of the process of the invention which is directed to the improved preparation of acylsulfamoylbenzamides, especially N-[4-(cyclopropylcarbamoyl)phenylsulfonyl]-2-methoxybenzamide, reference is made hereinafter to a specific means of production of the reactant of the formula (II), i.e. 4-[[(2-methoxybenzoyl)amino]sulfonyl]benzoyl chloride.

An improved process for preparing the reactant of the formula (II) is described in international patent application PCT/EP2014/071388 and is incorporated into the present description hereinafter to promote the enablement of the present invention. The aforementioned process relates to the preparation of 4-[[(benzoyl)amino]sulfonyl]benzoyl chlorides of the formula (II)

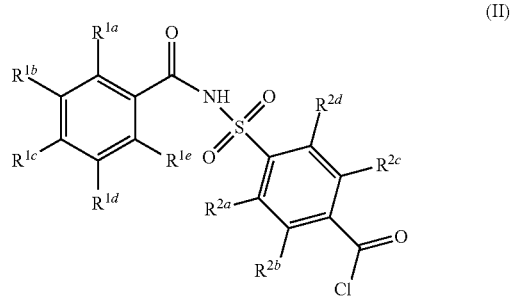

(II)

in which the $R^{1a}$ to $R^{1e}$ radicals and the $R^{2a}$ to $R^{2d}$ radicals are each independently selected from the group consisting of hydrogen, halogen, $(C_1-C_6)$-alkyl, $(C_1-C_6)$-haloalkyl, $(C_1-C_6)$-alkoxy, $(C_3-C_7)$-cycloalkyl, $(C_1-C_6)$-alkylthio, $(C_3-C_7)$-cycloalkylthio, $S(O)_q$—$(C_1-C_6)$-alkyl with q=0, 1 or 2, $(C_1-C_6)$-alkylcarbonyl, —CO-aryl, cyano and nitro or in which two adjacent $R^{1a}$ to $R^{1e}$ radicals in each case form a —O—CH$_2$CH$_2$— radical,
proceeding from a compound of the formula (III)

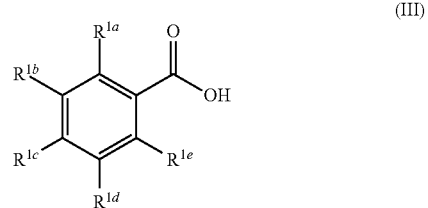

(III)

in which the $R^{1a}$ to $R^{1e}$ radicals are each as defined above, and
a compound of the formula (IV)

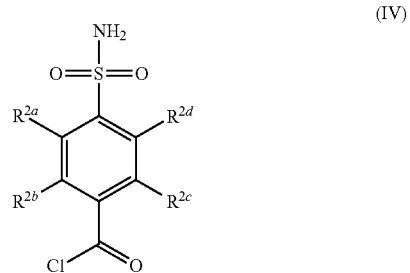

(IV)

in which the $R^{2a}$ to $R^{2d}$ radicals are each as defined above, where the compounds of the formula (III) and (IV) as reactants are converted
  in a solvent selected from the group of the aprotic polar solvents, or
  in a solvent composition comprising at least one solvent selected from the group of the aprotic polar solvents.

The aforementioned process is preferably employable for preparation of compounds of the formula (II) in which the $R^{1a}$ to $R^{1e}$ and $R^{2a}$ to $R^{2d}$ radicals are independently selected from the group consisting of
hydrogen, fluorine, chlorine, bromine,
($C_1$-$C_6$)-alkyl, where the alkyl radical is branched or unbranched and is unsubstituted or substituted by one or more substituents selected from the group consisting of ($C_1$-$C_4$)-alkoxy and ($C_3$-$C_7$)-cycloalkyl,
($C_1$-$C_6$)-haloalkyl, where the alkyl radical is unsubstituted or substituted by one or more substituents selected from the group consisting of fluorine, chlorine, bromine and iodine,
($C_3$-$C_7$)-cycloalkyl, where the cycloalkyl radical is unsubstituted or substituted by one or more substituents selected from the group consisting of ($C_1$-$C_4$)-alkyl and ($C_3$-$C_7$)-cycloalkyl and ($C_1$-$C_4$)-alkoxy,
($C_1$-$C_6$)-alkoxy, where the alkoxy radical is branched or unbranched and is unsubstituted or substituted by one or more substituents selected from the group consisting of ($C_1$-$C_4$)-alkoxy and ($C_3$-$C_7$)-cycloalkyl,
($C_3$-$C_7$)-cycloalkoxy, where the cycloalkoxy radical is unsubstituted or substituted by one or more substituents selected from the group consisting of ($C_1$-$C_4$)-alkyl and ($C_1$-$C_4$)-alkoxy,
($C_1$-$C_6$)-alkylthio, where the alkylthio radical is branched or unbranched and is unsubstituted or substituted by one or more substituents selected from the group consisting of ($C_1$-$C_4$)-alkyl and ($C_1$-$C_4$)-alkoxy,
($C_3$-$C_7$)-cycloalkylthio, where the cycloalkylthio radical is unsubstituted or substituted by one or more substituents selected from the group consisting of ($C_1$-$C_4$)-alkyl and ($C_1$-$C_4$)-alkoxy, where
the process is more preferably employable for preparation of compounds of the formula (II) in which the $R^{1a}$ radical is an unsubstituted ($C_1$-$C_4$)-alkoxy radical.

Particular preference is given to the employment of the aforementioned process for preparation of 4-[[(2-methoxybenzoyl)amino]sulfonyl]benzoyl chloride, i.e. particular preference is given to the inventive conversion of that compound of the formula (II) in which the $R^{1a}$ radical is methoxy (—O—CH$_3$) and, at the same time, the $R^{1b}$ to $R^{1e}$ radicals are each hydrogen (H).

It is also elucidated hereinafter that higher dimer formation is found in the case of use of the commonly used toluene and chlorobenzene solvents for preparation of N-[4-(cyclopropylcarbamoyl)phenylsulfonyl]-2-methoxybenzamides than in the case of use of an aprotic polar solvent. The advantages of the use of aprotic polar solvents are apparent in the overview from Table 1 below and the analysis thereof which follows.

It is found that the exchange of the solvents for an aprotic polar solvent can simultaneously also avoid various problems associated with dimer formation.

These subsequent problems include filtration problems at the amide chloride stage, i.e. the filtration of the reaction solution that arises in the preparation of 4-[[(2-methoxybenzoyl)amino]sulfonyl]benzoyl chloride is found to be difficult in practice. A further problem is the reduction in the yield both for the amide chloride preparation stage and for the cyprosulfamide preparation stage and the simultaneous deterioration in the quality, i.e. the purity, of both products.

The problems mentioned can be avoided through the use of aprotic polar solvents.

Aprotic polar (dipolar) solvents are chemical compounds which are notable in that they do not eliminate any protons and are simultaneously polar.

In a formal sense, carboxylic esters are also assigned in the literature to the group of the aprotic nonpolar solvents to some degree, in spite of their polarity. In connection with the present invention, therefore, it is stated for reasons of clarity that, in the case of the present invention, carboxylic esters, especially the esters of propionic acid and of acetic acid, for example isopropyl acetate, are counted as part of the group of the aprotic polar solvents. The chlorobenzene solvent, in contrast, in spite of its high dipole moment, is hydrophobic in water and thus barely soluble, i.e. chlorobenzene is nonpolar. Toluene also forms part of the group of the nonpolar solvents.

It can be stated that specifically aprotic and simultaneously polar solvents suppress the formation of dimers in amide chloride preparation, and so it is possible by virtue of the improved reaction regime to obtain compounds of the formula (II) with higher yields.

The aprotic polar compounds suitable as solvents in accordance with the invention have to be chemically stable and distillable and should also have a molar mass (molecular weight) below 200. Because of the upper limit on the molecular weight, these solvents are characterized by a comparatively low boiling point. Thus, the selection of the useful solvents simultaneously fixes an upper limit for the reaction temperature. This upper temperature limit simultaneously exerts an assurance function and constitutes an additional advantage in the case of the implementation of the preparation process on the technical and industrial scale with regard to the reaction regime.

TABLE 1

Tabular comparison of the yields on the basis of HPLC analysis in the case of use of different solvents for preparation of compounds of the formula (II), i.e. for preparation of 4-[[(benzoyl)amino]sulfonyl]benzoyl chlorides.

| | | Chlorinating agent | Reaction time | | Yield | | | Wash water | Dimers * Solids | |
|---|---|---|---|---|---|---|---|---|---|---|
| | | Thionyl | | Further | | | | | | |
| Exp. No. | Solvent | chloride mol. eq. | Reaction h | stirring h | Weight g | % by wt. | HPLC % of th. | Isolated % of th. | area % | % of th. |
| A1 | isopropyl acetate | 2.5 | 3.5 (80-90° C.) | 60 (90° C.) | 180.2 | 99.5 | 91.4 | 2.9 | 0.08 | 0.14 |
| A2 | isopropyl acetate | 2.5 | 7 (80-90° C.) | 0 | 190.4 | 98.4 | 95.0 | 1.0 | 0.10 | 0.18 |

TABLE 1-continued

Tabular comparison of the yields on the basis of HPLC analysis in the case of use of different solvents for preparation of compounds of the formula (II), i.e. for preparation of 4-[[(benzoyl)amino]sulfonyl]benzoyl chlorides.

| | | Chlorinating agent | Reaction time | | | | Yield | | Dimers * | |
| | | Thionyl | | Further | | | | Wash | Solids | |
| Exp. No. | Solvent | chloride mol. eq. | Reaction h | stirring h | Weight g | % by wt. | % of th. | water % of th. | area % | % of th. |
| --- | --- | --- | --- | --- | --- | --- | --- | --- | --- | --- |
| A3 | isopropyl acetate | 2.5 | 7 (80-90° C.) | 0 | 192.3 | 96.5 | 95.7 | 1.5 | 0.10 | 0.19 |
| A4 | isopropyl acetate | 2.5 | 7 (80-90° C.) | 0 | 192.7 | 99.1 | 98.4 | 1.3 | 0.35 | 0.67 |
| B1 | toluene | 2.5 | 5 (85° C.) | 1 (85° C.) | 162.5 | 96.4 | 88.6 | 3.1 | 1.05 | 1.85 |
| B2 | toluene | 2.5 | 7 (85° C.) | 1 (85° C.) | 155.8 | 95.3 | 83.9 | 3.1 | 1.64 | 2.77 |
| B3 | toluene | 3 | 4 (110° C.) | 0 | 161.9 | 95.9 | 88.7 | 3.9 | 1.09 | 1.93 |
| C1 | chloro-benzene | 3 | 4 (85-90° C.) | 12 (85-90° C.) | 150.2 | 88.2 | 75.6 | 8.3 | 5.87 | 9.65 |
| C2 | chloro-benzene | 3 | 4 (85-90° C.) | 12 (85-90° C.) | 143.9 | 89.9 | 73.9 | 10.0 | 5.68 | 8.94 |
| C3 | chloro-benzene | 3 | 4 (85-90° C.) | 0 | 153.6 | 96.7 | 84.8 | 8.1 | 1.57 | 2.64 |

* Factor of 1.5

The above table compares the isopropyl acetate solvent used in accordance with the invention with the toluene and chlorobenzene solvents with homogeneous use of thionyl chloride as chlorinating agent and with a reaction time of several hours in each case and with reaction temperatures within a narrow range.

Comparison of Yields

The tabular comparison demonstrates firstly, through experiments A2, A3, A4 and B3 and experiment C3, that the yields of the reaction are higher for all solvents if no further stirring of the reaction solution takes place. In industrial production, however, further stirring of the reaction solution frequently cannot be avoided for technical reasons.

For instance, the table demonstrates, through experiments A1 and B2 and experiments C1 and C2, that even further stirring of the reaction solution for one hour after a reaction time of several hours (i.e. after a reaction time of 3.5 hours to 7 hours) distinctly worsens the yield of the reaction. Only experiment B1 forms an exception and does not confirm that a reduction in the yield has to be expected even in the case of further stirring for just one hour.

In addition, in the comparison of the various solvents, it is noticeable that the deterioration in the yield is comparatively small in spite of an extremely long further stirring time of 60 hours (experiment A1) when isopropyl acetate is used as solvent and the yield is nevertheless above 90%, namely 91.4%. In comparison, the yield when the toluene and chlorobenzene solvents are used is below 90% in both cases, namely 88.7% (experiment B3) and 84.8% (experiment C3), with no further stirring in the two latter experiments. If there is further stirring in the case of use of the toluene and chlorobenzene solvents, the yield is even worse, namely, for example, 83.9% (experiment B2) and 73.9% (experiment C2).

Comparison of Dimer Formation

A particular advantage of the process of the invention is found to be the low level of dimer formation when isopropyl acetate is used as solvent.

Experiments A2 and A3 demonstrate, in comparison to experiment A1, that, when isopropyl acetate is used as solvent, even an extremely long further stirring time of 60 hours (experiment A1) does not have any significant effect on the unwanted dimer formation.

An exception is formed by experiment A4 with a value of 0.67. However, the value of 0.67 is still much lower than the corresponding values in the case of use of toluene and chlorobenzene as solvents. The corresponding values in the case of use of toluene and chlorobenzene are in the range of 1.85 to 9.65. Dimer formation is noticeably high when chlorobenzene is used as solvent with further stirring for several hours (cf. experiments C1 and C2).

In summary, it can be stated in relation to Table 1 that, in the case of comparative use of one of the solvents of the invention, namely in the case of use of isopropyl acetate in comparison with toluene and chlorobenzene, the improvement in the yield is unexpectedly high and, at the same time, the unwanted dimer formation is surprisingly low.

Thus, the use of isopropyl acetate is advantageous in two ways and enables a robust process which is particularly suitable and advantageous for industrial use for economic reasons as well because of the potential for savings of various resources.

In the above-defined group of aprotic and simultaneously polar solvents, particular aprotic polar solvents are preferred in the performance of the process of the invention.

Preferred classes of aprotic polar solvent are open-chain ketones, cyclic ketones, esters, amides, nitriles or ethers, each of which are unsubstituted or substituted, where the particular solvent molecules are unsubstituted or substituted by one or more substituents selected from the group consisting of fluorine, chlorine, bromine, iodine, and $(C_1-C_4)$-alkyl.

Preferably, the conversion of the reactants of the formula (III) and the formula (IV) is effected in a mixture of aprotic polar solvents each having a molecular weight of below 200, the mixture comprising at least two or more solvents selected from the group consisting of cyclohexanone, methyl isobutyl ketone, diisobutyl ketone, ethyl acetate, propyl acetate, butyl acetate, isopropyl acetate, isobutyl acetate, ethyl propionate, ethyl butyrate, propyl propionate, isopropyl propionate, dialkylacetamide, cycloalkylacetamide, acetonitrile, propionitrile, butyronitrile, valeronitrile, methyl tert-butyl ether, tetrahydrofuran and methyltetrahydrofuran.

More preferably, the conversion of the reactants of the formula (III) and the formula (IV) is effected exclusively in a specific solvent, the solvent being selected from the group consisting of cyclohexanone, methyl isobutyl ketone, diisobutyl ketone, ethyl acetate, propyl acetate, butyl acetate, isopropyl acetate, isobutyl acetate, ethyl propionate, ethyl butyrate, propyl propionate, isopropyl propionate, dialkylacetamide, cycloalkylacetamide, acetonitrile, propionitrile, butyronitrile, valeronitrile, methyl tert-butyl ether, tetrahydrofuran and methyltetrahydrofuran. Most preferably, the two solvents are isopropyl acetate and isobutyl acetate.

It is likewise possible that the conversion of the reactants of the formula (III) and the formula (IV) is not effected in just one specific aprotic polar solvent but in a mixture of various solvents. In this case, the solvent composition comprises at least two solvents each selected from the group consisting of cyclohexanone, methyl isobutyl ketone, diisobutyl ketone, ethyl acetate, propyl acetate, butyl acetate, isopropyl acetate, isobutyl acetate, ethyl propionate, ethyl butyrate, propyl propionate, isopropyl propionate, dialkylacetamide, cycloalkylacetamide, acetonitrile, propionitrile, butyronitrile, valeronitrile, methyl tert-butyl ether, tetrahydrofuran and methyltetrahydrofuran.

Very particularly preferably, the conversion of the reactants of the formula (III) and the formula (IV) is effected in a solvent selected from the group of the carboxylic esters or in a solvent composition comprising at least two solvents selected from the group of the carboxylic esters.

Another significant advantage of the use of carboxylic esters as solvent is that the recovery thereof is less complex than the recovery of an aromatic solvent, for example the recovery of chlorobenzene or toluene. The improved solvent recovery distinctly reduces the amounts of waste overall in the interests of sustainability.

However, the most important advantage is that the formation of dimers is avoided when the reaction is performed in a carboxylic ester or a carboxylic ester mixture as solvent.

Most preferred is the conversion of the reactants of the formula (III) and the formula (IV) in a solvent selected from the group consisting of isopropyl acetate, isobutyl acetate and ethyl propionate or in a solvent composition comprising at least two solvents selected from the group consisting of isopropyl acetate, isobutyl acetate and ethyl propionate.

If the conversion is effected in just one solvent, isopropyl acetate is the solvent of best suitability. In the case of use of isopropyl acetate as solvent, the compound of the formula (II) can be prepared with a particularly good yield and good quality by conversion of the reactants of the formula (III) and the formula (IV).

As a further advantage of isopropyl acetate, it has also been found that, when isopropyl acetate is used as solvent, the recovery of the chlorinating agent used in excess in the reaction is particularly efficient. This is in the interests of the environment and is also important for reasons of cost.

Usable chlorinating agents in connection with the process of the invention are in principle any chlorinating agents known to be suitable to those skilled in the art, and it is also conceivable that a mixture consisting of a plurality of different chlorinating agents is used.

Preferred chlorinating agents are selected from the group of the sulfur- and phosphorus-based chlorinating agents. These include thionyl chloride, phosphorus oxychloride or phosphorus pentachloride, or carbon-based chlorinating agents such as oxalyl chloride or phosgene. The latter are usable for conversion of a carboxylic acid to a corresponding acid chloride.

Particularly preferred chlorinating agents are $Cl_2$, $SO_2Cl_2$, $SOCl_2$ (thionyl chloride), N-chlorosuccinimide, the most preferred chlorinating agent being thionyl chloride. Also conceivable is the use of a mixture consisting of at least two of the aforementioned chlorinating agents.

Further usable chlorinating agents, in each case alternatively or in combination, are silicon tetrachloride, trichloromethylsilane, dichloromethylsilane, trichlorophenylsilane, aluminum trichloride, boron trichloride, titanium tetrachloride, tin tetrachloride, zinc dichloride or bismuth trichloride, or a mixture thereof. It is also possible to use mixtures of halosilanes and aluminum trichloride or zinc dichloride, for example mixtures of silicon tetrachloride and aluminum trichloride, in which case aluminum trichloride or zinc dichloride serve as catalyst and are used in amounts of 1% to 3% by weight, based on silicon tetrachloride.

In the performance of the process of the invention, between 2.5 and 3.0 equivalents of exchangeable chlorine atoms in a chlorinating agent or chlorinating agent mixture are used per equivalent of the formula (III or IV). Preference is given to using 2.5 equivalents of thionyl chloride.

The compounds of the formula (III) and (IV) are used in equimolar amounts.

The use of a catalyst is advantageously not required in the reaction of the invention.

In the performance of the process of the invention, the reaction temperatures may be varied within the ranges stipulated hereinafter. In general, temperatures employed are in the range from 20° C. to 90° C. Preference is given to temperatures in the range from 40° C. to 90° C. Particular preference is given to temperatures in the range from 80° C. to 90° C.

The process according to the invention is generally performed under atmospheric pressure. However, it is also possible to work under elevated or reduced pressure. The preferred pressure range for the performance of the reaction of the invention is between 0.1 bar and 10 bar.

Synthesis Example

Preparation of Cyprosulfamide Proceeding from 4-[[(2-methoxybenzoyl)amino]sulfonyl]benzoyl chloride 1.8 l/eq of water and 0.10 eq. (equivalents) of cyclopropylamine are initially charged at about 20° C. (A maximum of 0.10 eq. of cyclopropylamine (CPA), i.e. ≤0.10 eq. of cyclopropylamine, is initially charged. The initially charged CPA may optionally originate from the recovery of the prior batch.)

4-[[(Methoxybenzoyl)amino]sulfonyl]benzoyl chloride (amide chloride) is added in portions (24 portions) at 20° C.-35° C. over a period of 4 h (4 hours). In parallel, 1.1 eq. of CPA are metered in in such a way that the pH is kept at 9.0-9.6. After about 20% of the amount of amide chloride, the amount of CPA has been metered in completely.

Thereafter, additionally in parallel, 2 eq. of 32% NaOH are metered in in such a way that the pH is kept at 9.2-9.8. After addition of about ⅔ of the amount of amide chloride, the product precipitates out.

On completion of addition of amide chloride and NaOH, the suspension is heated to 80° C. within 1 h (this gives a cloudy solution).

Then the excess CPA is distilled off at 80° C. and 400-300 mbar (the CPA/water mixture can be reused again).

For precipitation of the product (to improve the pumpability of the product), water is added and the mixture is acidified to pH 5.8-6.2 at 80° C. with about 1 eq. of 10% hydrochloric acid within 3 h.

The suspension is stirred at 80° C. and about pH 6 for 30 minutes and then cooled down to 20° C. to 30° C. In the course of this, the pH is readjusted to about pH 6 with 10% hydrochloric acid. The suspension is filtered through a suction filter. The filter cake is washed with water and crushed dry. The solid is dried at 45° C. and less than 50 mbar. The yield is 98.7% of theory (content: 98.8% (HPLC against standard)).

The invention claimed is:

1. A process for preparing a compound of formula (Ia)

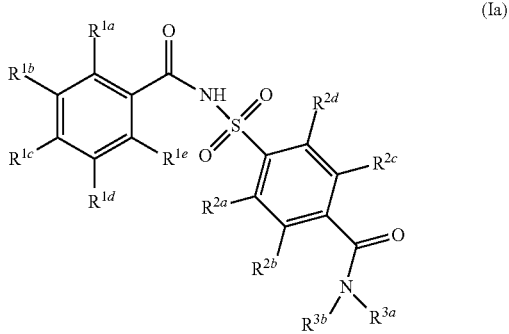

(Ia)

in which
R$^{1a}$ to R$^{1e}$ and R$^{2a}$ to R$^{2d}$ are each independently selected from the group consisting of hydrogen, halogen, (C$_1$-C$_6$)-alkyl, (C$_1$-C$_6$)-haloalkyl, (C$_1$-C$_6$)-alkoxy, (C$_3$-C$_7$)-cycloalkoxy, (C$_3$-C$_7$)-cycloalkyl, (C$_1$-C$_6$)-alkylthio, (C$_3$-C$_7$)-cycloalkylthio, S(O)$_q$—(C$_1$-C$_6$)-alkyl with q=0, 1 or 2, (C$_1$-C$_6$)-alkylcarbonyl, —CO-aryl, cyano and nitro or in which two adjacent R$^{1a}$ to R$^{1e}$ radicals in each case form a —O—CH$_2$CH$_2$— radical, and
R$^{3a}$ is selected from the group consisting of hydrogen and the following radicals: (C$_1$-C$_6$)-alkyl, (C$_1$-C$_6$)-haloalkyl, (C$_3$-C$_7$)-cycloalkyl, (C$_1$-C$_6$)-alkoxy, (C$_1$-C$_6$)-alkylthio, (C$_3$-C$_7$)-cycloalkylthio, or —(CH$_2$)-heterocyclyl, wherein these are each unsubstituted or substituted by one or more substituents selected from the group consisting of halogen, (C$_1$-C$_6$)-alkyl, (C$_1$-C$_6$)-haloalkyl, (C$_1$-C$_6$)-alkoxy, cyano and nitro, and
R$^{3b}$ is selected from the group consisting of hydrogen and the following radicals: (C$_1$-C$_6$)-alkyl, (C$_2$-C$_6$)-alkenyl, (C$_2$-C$_6$)-alkynyl, (C$_1$-C$_6$)-alkoxy, (C$_2$-C$_6$)-alkenyloxy, or —(CH$_2$)-heterocyclyl, wherein these are each unsubstituted or substituted by one or more substituents selected from the group consisting of halogen, (C$_1$-C$_4$)-alkoxy and (C$_1$-C$_4$)-alkylthio, or
R$^{3a}$ and R$^{3b}$ together with the connecting nitrogen atom form a 3- to 8-membered, saturated or unsaturated ring, by reacting a compound of formula (II)

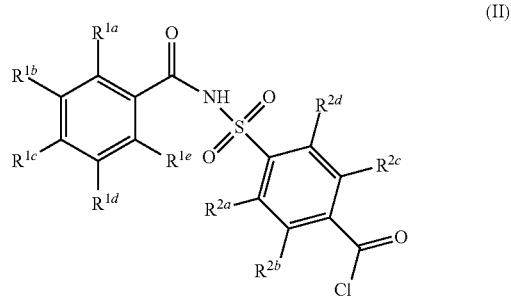

(II)

wherein R$^{1a}$ to R$^{1e}$ and R$^{2a}$ to R$^{2d}$ radicals are each as defined above, with an amine of the formula R$^{3a}$R$^{3b}$NH in which the R$^{3a}$ and R$^{3b}$ radicals are each as defined above, in aqueous solution, wherein the pH is regulated by
before adding the reactant of the formula (II), initially charging a portion of the amine of the formula R$^{3a}$R$^{3b}$NH in water at the start of the reaction to form an initial reaction charge, wherein the initial reaction charge does not include an alkali metal hydroxide solution, and
adding the remaining amount of the amine of the formula R$^{3a}$R$^{3b}$NH to the reaction mixture over the course of the reaction in one or more steps along with the reactant of the formula (II).

2. The process for preparing a compound of the formula (Ia) according to claim 1, wherein R$^{1a}$ to R$^{1e}$ and R$^{2a}$ to R$^{2d}$ are independently selected from the group consisting of hydrogen, fluorine, chlorine, bromine,
(C$_1$-C$_6$)-alkyl, wherein the alkyl radical is branched or unbranched and is unsubstituted or substituted by one or more substituents selected from the group consisting of (C$_1$-C$_4$)-alkoxy and (C$_3$-C$_7$)-cycloalkyl,
(C$_1$-C$_6$)-haloalkyl, wherein the the halogen substituents are selected from the group consisting of fluorine, chlorine, bromine and iodine,
(C$_3$-C$_7$)-cycloalkyl, wherein the cycloalkyl radical is unsubstituted or substituted by one or more substituents selected from the group consisting of (C$_1$-C$_4$)-alkyl, (C$_3$-C$_7$)-cycloalkyl and (C$_1$-C$_4$)-alkoxy,
(C$_1$-C$_6$)-alkoxy, wherein the alkoxy radical is branched or unbranched and is unsubstituted or substituted by one or more substituents selected from the group consisting of (C$_1$-C$_4$)-alkoxy and (C$_3$-C$_7$)-cycloalkyl,
(C$_3$-C$_7$)-cycloalkoxy, wherein the cycloalkoxy radical is unsubstituted or substituted by one or more substituents selected from the group consisting of (C$_1$-C$_4$)-alkyl and (C$_1$-C$_4$)-alkoxy,
(C$_1$-C$_6$)-alkylthio, wherein the alkylthio radical is branched or unbranched and is unsubstituted or substituted by one or more substituents selected from the group consisting of (C$_1$-C$_4$)-alkyl and (C$_1$-C$_4$)-alkoxy, and
(C$_3$-C$_7$)-cycloalkylthio, wherein the cycloalkylthio radical is unsubstituted or substituted by one or more substituents selected from the group consisting of (C$_1$-C$_4$)-alkyl and (C$_1$-C$_4$)-alkoxy.

3. The process for preparing a compound of the formula (Ia) according to claim 2, wherein R$^{1a}$ is an unsubstituted (C$_1$-C$_4$)-alkoxy radical and R$^{1b}$ to R$^{1e}$ and R$^{2a}$ to R$^{2d}$ are each hydrogen.

4. The process for preparing a compound of the formula (Ia) according to claim 3, wherein $R^{1a}$ is methoxy (—O—$CH_3$), and $R^{1b}$ to $R^{1e}$ and $R^{2a}$ to $R^{2d}$ are each hydrogen.

5. The process for preparing a compound of the formula (Ia) according to claim 1, wherein, in the formula (II),
$R^{1a}$ is methoxy (—O—$CH_3$) and $R^{1b}$ to $R^{1e}$ and $R^{2a}$ to $R^{2d}$ are each hydrogen and, in the
amine of the formula $R^{3a}R^{3b}NH$, the $R^{1a}$ radical is cyclopropyl and $R^{3b}$ is hydrogen.

6. The process for preparing a compound of the formula (Ia) according to claim 1, wherein the amine of the formula $R^{3a}R^{3b}NH$ initially charged in water at the start of the reaction is present in sufficient amount to bring about adjustment of the pH of the initial reaction charge to no more than 11.5.

7. The process for preparing a compound of the formula (Ia) according to claim 6, wherein the addition of the amount of the amine of the formula $R^{3a}R^{3b}NH$ which is not initially charged at the start of the reaction is effected in several steps, such that the pH during the addition is in the range from 7 to 10.5.

8. The process for preparing a compound of the formula (Ia) according to claim 7, wherein the addition of the amount of the amine of the formula $R^{3a}R^{3b}NH$ which is not initially charged at the start of the reaction is effected in several steps, such that the pH during the addition is in the range from 9 to 10.5.

9. The process for preparing a compound of the formula (Ia) according to claim 6, wherein after the formation of the initial reaction charge, a base selected from the group consisting of NaOH, KOH, $Ca(OH)_2$ and the group of the tertiary amines is added to the reaction mixture in order to prevent the pH from dropping below 8.

10. The process for preparing a compound of the formula (Ia) according to claim 9, wherein the base is NaOH, and the addition of the base NaOH keeps the pH in the range from 9 to 10.

11. The process for preparing a compound of the formula (Ia) according to claim 1, wherein the remaining amount of the amine of the formula $R^{3a}R^{3b}NH$ is added to reaction mixture over the course of the reaction in one or more steps in parallel with the compound of the formula (II).

12. The process for preparing a compound of the formula (Ia) according to claim 1, wherein the compound of the formula (II) is added by metered addition over a period of about 4 hours.

13. The process for preparing a compound of the formula (Ia) according to claim 9, wherein the base is added to the reaction mixture on completion of addition of the amine of the formula $R^{3a}R^{3b}NH$ and after addition of 20% of the compound of the formula (II), or on completion of addition of the compound of the formula (II).

14. The process for preparing a compound of the formula (Ia) according to claim 1, wherein the remaining amount of the amine of the formula $R^{3a}R^{3b}NH$ and the compound of the formula (II) are added to reaction mixture until 1:1 equivalents, based on the amount of amide chloride compound of the formula (II), is attained.

* * * * *